US00PP27529P2

(12) United States Plant Patent
Delabroye

(10) Patent No.: US PP27,529 P2
(45) Date of Patent: Jan. 3, 2017

(54) ***HEUCHERA* PLANT NAMED 'VAN GOGH'**

(50) Latin Name: ***Heuchera* hybrid**
Varietal Denomination: Van Gogh

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 72 days.

(21) Appl. No.: 14/121,863

(22) Filed: Oct. 28, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Bloembollen isie *Heuchera* series Master Painters at Plantarium Aug. 16, 2012, retrieved on Mar. 23, 2016, retrieved from the Internet at <http://www.bloembollenvisie.nl/Nieuws/Paginas/HeucheraserieMasterPainters%E2%84%A2opPlantarium.aspx#.VvKD6vlVgnE> 2 pp.*

Bloembollen isis Google English translation 1 page.*

Burton—*Heuchera* 'Van Gogh'—Just Lovely . . . Ready . . . Facebook, Jul. 28, 2013, retrieved on Mar. 23, 2016, retrieved from the Internet at <https://en-gb.facebook.com/heucheraholics/posts/10151713548547114> 1 page.*

Bloembollen isis Google English translation 2016, original document 2012, 1 page.*

* cited by examiner

*Primary Examiner* — June Hwu

(74) *Attorney, Agent, or Firm* — Penny J. Aguirre

(57) ABSTRACT

A new cultivar of hybrid *Heuchera* named 'Van Gogh', that is characterized by its compact plant habit with small leaves, its leaves that are yellow-green in color with red veins, its abundance of flowering stems extending straight up from the basal rosettes, and its deep pink flowers on dark red flowering stems.

2 Drawing Sheets

Botanical classification: *Heuchera* hybrid.
Cultivar designation: 'Van Gogh'.

BACKGROUND OF THE INVENTION

The present invention relates to a new and distinct cultivar of *Heuchera* of hybrid origin, botanically known as a *Heuchera* and is hereinafter referred to by its cultivar name 'Van Gogh'.

The new cultivar was discovered as a chance seedling in a trial field by the Inventor in Hantay, France in April of 2011. The trial field contained hundreds of cultivars and proprietary seedlings of *Heuchera* from the Inventor's breeding program. The exact parentage of 'Van Gogh' is therefore unknown.

Asexual propagation of the new cultivar was first accomplished under the direction of the Inventor by in vitro propagation initiated from meristem tissue in Rijswijk, The Netherlands in June of 2012. Asexual propagation of the new cultivar by in vitro propagation has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Van Gogh' as a new and unique cultivar of *Heuchera*.

1. 'Van Gogh' exhibits a compact plant habit with small leaves.
2. 'Van Gogh' exhibits leaves that are yellow-green in color with red veins.
3. 'Van Gogh' exhibits an abundance of tall flowering stems extending straight up from the basal rosettes.
4. 'Van Gogh' exhibits deep pink flowers on dark red flowering stems.

'Van Gogh' can be most closely compared to the *Heuchera* cultivars 'Circus' (U.S. Plant Pat. No. 25,495) and 'Tiramisu' (U.S. Plant Pat. No. 20,429). 'Circus' differs from 'Van Gogh' in having a less compact plant habit, in having young leaves that are less golden-yellow in color, and in having flowers that are lighter pink in color. 'Tiramisu' is similar to 'Van Gogh' in foliage coloration. 'Tiramisu' differs from 'Van Gogh' in having a less compact plant habit, in having less contrasting colors between the leaf blade and veins, and in having flowers that are white in color.

BRIEF DESCRIPTION OF THE DRAWINGS

The accompanying colored photographs illustrate the overall appearance and distinct characteristics of the new *Heuchera*. The photographs were taken of a plant three-years in age as grown in a garden bed in a poly covered unheated greenhouse in Hillegom, The Netherlands. The plant was placed in a container for the photograph.

The photograph in FIG.1 provides a side view of the plant habit of 'Van Gogh' in bloom.

Figure 1:
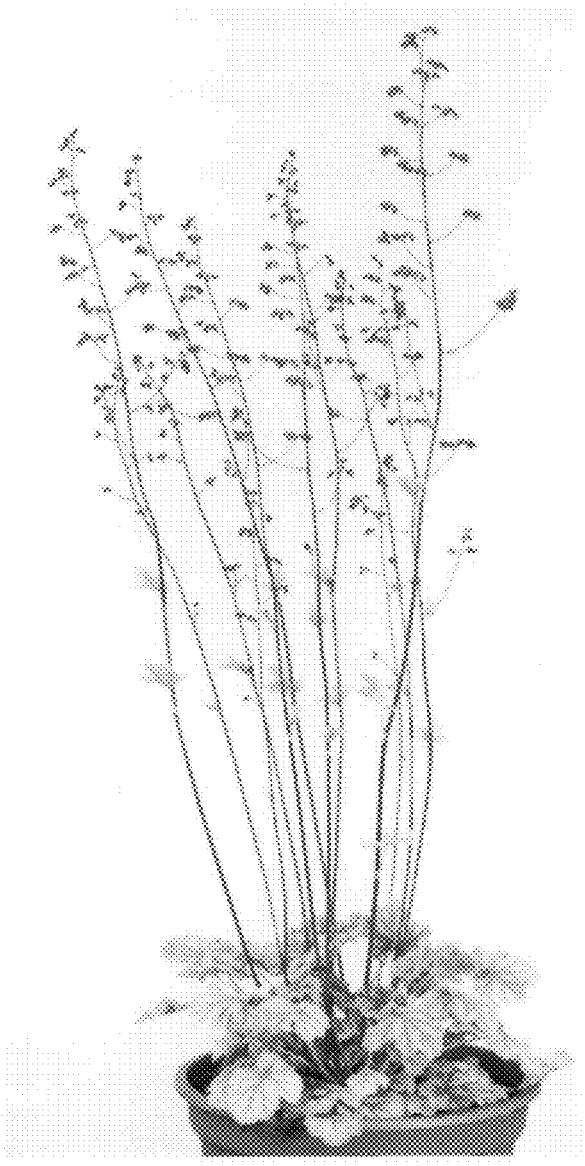
Figure 2:
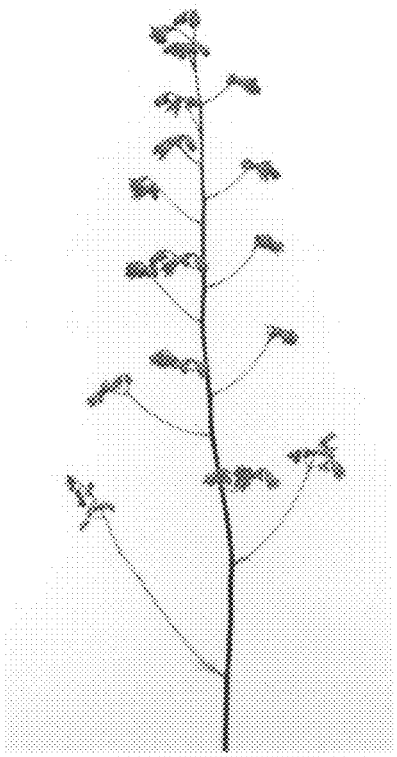

The photograph in FIG. 2 provides a close-up view of an inflorescence of 'Van Gogh'.

Figure 3:
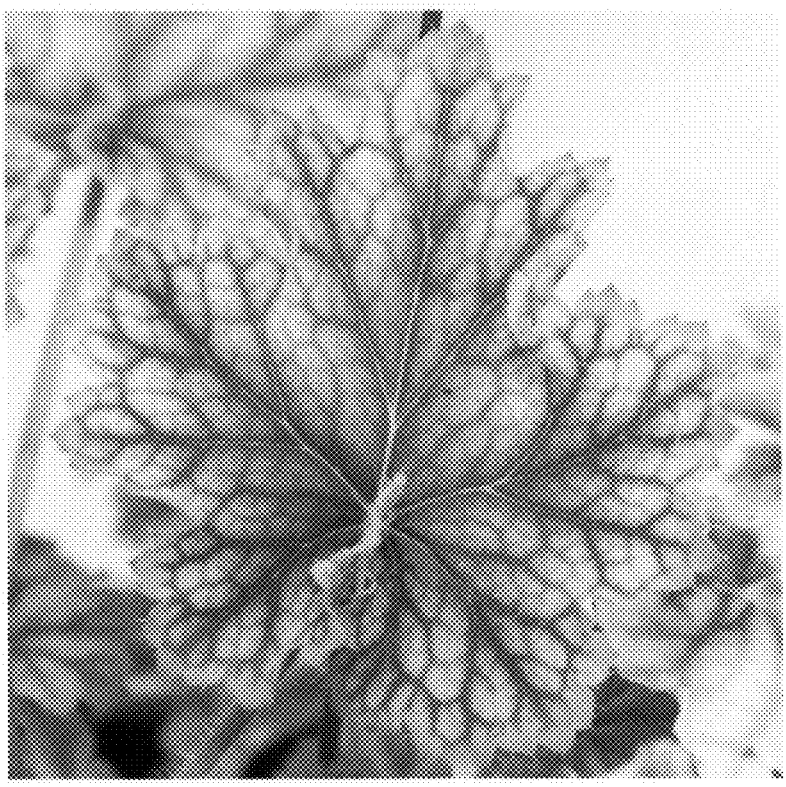

The photograph in FIG. 3 provides a close-up view of a leaf of 'Van Gogh'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of three year-old plants of 'Van Gogh' as grown in a garden bed in a poly covered unheated greenhouse in Hillegom, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—An average of 4 weeks from late spring into summer in The Netherlands.

*Plant type.*—Herbaceous perennial.

*Plant habit.*—Compact, clump-forming.

*Height and spread.*—An average of 80 cm in height (including inflorescences, 25 cm from base to apex of inflorescence) and 35 cm in width in three years in the garden.

*Hardiness.*—At least in U.S.D.A. Zones 3 to 9.

*Diseases and pests.*—No particular susceptibility or resistance to pests and diseases has been observed.

*Root description.*—Fibrous roots on woody rootstalks.

*Propagation.*—In vitro propagation.

*Growth rate.*—Moderate.

Stem description (peduncle, flowering stem):

*Shape.*—Round.

*Stem color.*—187C.

*Stem size.*—Primary; an average of 2.5 mm in diameter and 71 cm in length, secondary; an average of 0.75 mm in diameter and 3.5 cm in length.

*Stem strength.*—Moderate.

*Stem aspect.*—Average angle of primary peduncle; 82.5° (horizontal=0°), average angle of secondary peduncles; 85° to primary peduncle (=0°).

*Stem surface.*—Densely covered with very short hairs an average of 1 mm in length and NN155A in color.

*Stem number.*—Average of 15 flowering stems.

*Branching habit.*—Flowering stems emerge from basal rosette.

Foliage description:

*Leaf shape.*—Broad ovate to orbicular.

*Leaf division.*—Simple.

*Leaf base.*—Hastate, moderately overlapping.

*Leaf apex.*—Rounded with tip mucronate.

*Leaf venation.*—Laciniate, color; young leaves; 178A on upper surface and 144D on lower surface; mature leaves upper surface; a blend between 150C and 154D with tertiary veins 176C to 176D and lower surface, lower surface main and secondary veins are sparsely covered with short hairs; an average of 0.5 mm in length and NN155A in color.

*Leaf margins.*—Lobed with average of 7 lobes per leaf, medium lobe depth, lobe margins crenate and weakly undulate, moderately to densely covered with short hairs an average of 0.5 mm in length and NN155A in color.

*Leaf attachment.*—Petiolate.

*Leaf arrangement.*—Alternate in basal rosettes.

*Leaf orientation.*—Typically nearly horizontal to petiole and slightly cupped.

*Leaf surface.*—Upper surface; dull and moderately covered with short hairs an average of 0.5 mm in length and NN155A in color, lower surface; dull and moderately to densely covered with short hairs an average of 0.5 mm in length and NN155A in color.

*Leaf color.*—In the spring, young leaves upper surface; 150B to 150C with margins 150A and area surrounding veins 176B to 176D, and lower surface; 151D with area surrounding veins 182B to 182C, in the summer and fall, mature leaves upper surface; a blend between 150C and 154D with margins 151C to 151D and area surrounding veins 176D, lower surface; 154C with area surrounding veins 182C to 182D.

*Leaf size.*—An average of 6.5 cm in length and 6.4 cm in width.

*Leaf quantity.*—An average of 18 per basal rosette.

*Petioles.*—An average of 13.6 cm in length and 2 mm in diameter, color; 144C to 144D and suffused with 176D, surface densely covered with very short hairs; an average of 1 mm in length and NN155A in color.

*Stipules.*—Small leafy stipules at the base of each leaf, narrow acute apex, an average of 1.3 cm in length and 2.5 mm in width, color; 145D.

Flower description:

*Inflorescence type.*—Numerous small bell-shaped flowers arranged on panicles on peduncles emerging from the base of the rosette.

*Inflorescence size.*—An average of 26.8 cm in height and 9.8 cm in width.

*Inflorescence number.*—An average of 15 (three year-old plant).

*Flower fragrance.*—None.

*Flower quantity.*—Average of 130 flowers per flowering stem.

*Flower lastingness.*—Average of one week.

*Flower buds.*—Obovate in shape, an average of 5 mm in diameter and 2.5 mm in diameter, color; 52A with a blend between 53A and 59A towards the top.

*Flower attitude.*—Outwards to slightly drooping downwards.

*Flower type.*—Single, campanulate.

*Flower size.*—About 9 mm in length and 6 mm in diameter.

*Petals.*—About 5, rotate arrangement and implanted in the hypanthium at base, narrow elliptic to narrow ovate and oblanceolate in shape, margin is entire, narrow acute apex acute, upper and lower surface is dull and glabrous, color of upper and lower surface when opening and when fully open; N57A, an average of 3 mm in length and 1 mm in width.

*Calyx.*—Campanulate, sepals fused to hypanthium, 9 mm in length and 6 mm in diameter.

*Sepals.*—An average of 5, fused into campanulate hypanthium, elliptic in shape, an average of 9 mm in length and 2.5 mm in width, margin is entire and fused into hypanthium, acute apex, fused base, color; immature upper and lower surface; 52A with apex a blend between 53A and 59A, mature upper and lower surface; 58B with 60A towards the tip, surfaces are dull, upper and lower surfaces are densely covered with very short glandular hairs an average of 0.1 mm in length and matched to the sepals in color.

*Pedicels.*—An average of 2 mm in length and 0.5 mm in diameter, 187A in color, moderate strength, average angle of main flower pedicel 0° (0°=horizontal), average angle of secondary flower pedicels 30° to main pedicel.

Reproductive organs:

*Gynoecium.*—An average of 2 pistils, 2.5 mm in length, stigma; pointed in shape, 155D in color, style; an average of 2 mm in length and 155D in color, ovary; 151D in color.

*Androcoecium.*—An average of 5 stamens, anthers; ovate in shape, about 0.5 mm in length and 202A in color, filament; 1.5 mm in length and NN155C to NN155D in color, pollen; none detected.

*Seed/fruit.*—No fruit or seeds were observed.

It is claimed:

1. A new and distinct cultivar of hybrid *Heuchera* plant named 'Van Gogh' as herein illustrated and described.

* * * * *